United States Patent
Khuntia et al.

(10) Patent No.: US 10,814,144 B2
(45) Date of Patent: Oct. 27, 2020

(54) RADIATION TREATMENT BASED ON DOSE RATE

(71) Applicant: Varian Medical Systems, Palo Alto, CA (US)

(72) Inventors: Deepak Khuntia, Los Altos, CA (US); Edward Vertatschitsch, San Carlos, CA (US); Eric Abel, San Jose, CA (US); Anthony Magliari, Newark, IL (US); Christel Smith, Santa Barbara, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 27 days.

(21) Appl. No.: 16/294,707

(22) Filed: Mar. 6, 2019

(65) Prior Publication Data
US 2020/0282232 A1    Sep. 10, 2020

(51) Int. Cl.
*A61N 5/10* (2006.01)

(52) U.S. Cl.
CPC .......... *A61N 5/1031* (2013.01); *A61N 5/1043* (2013.01); *A61N 5/1045* (2013.01); *A61N 2005/1034* (2013.01); *A61N 2005/1035* (2013.01); *A61N 2005/1087* (2013.01)

(58) Field of Classification Search
CPC .... A61B 2090/0445; A61B 2090/0481; A61N 5/103; A61N 5/10; A61N 5/1048; A61N 5/1077; A61N 2007/0056; A61N 5/1017
See application file for complete search history.

(56) References Cited

U.S. PATENT DOCUMENTS

| | | |
|---|---|---|
| 2008/0023644 A1 | 1/2008 | Pedroni |
| 2009/0063110 A1 | 3/2009 | Failla et al. |
| 2009/0287467 A1 | 11/2009 | Sparks et al. |
| 2010/0119032 A1 | 5/2010 | Yan et al. |
| 2010/0177870 A1 | 7/2010 | Nord et al. |
| 2011/0060602 A1* | 3/2011 | Grudzinski ............ G06Q 50/22 705/2 |
| 2011/0135058 A1 | 6/2011 | Sgouros et al. |
| 2012/0076271 A1 | 3/2012 | Yan et al. |
| 2012/0197058 A1 | 8/2012 | Shukla et al. |
| 2013/0116929 A1 | 5/2013 | Carlton et al. |
| 2013/0150922 A1 | 6/2013 | Butson et al. |
| 2013/0177641 A1 | 7/2013 | Ghoroghchian |
| 2014/0206926 A1 | 7/2014 | Van Der Laarse |
| 2018/0207425 A1 | 7/2018 | Carlton et al. |
| 2018/0311509 A1 | 11/2018 | Sjolund et al. |
| 2019/0060667 A1 | 2/2019 | Vanderstraeten et al. |

OTHER PUBLICATIONS

Mark Podesta et al., "Dose Rate Mapping of VMAT Treatments", Physics in Medicine and Biology, May 10, 2016 (May 10, 2016), pp. 4048-4060, vol. 61, No. 11, Institute of physics Publishing, Bristol, GB.

* cited by examiner

*Primary Examiner* — Don K Wong

(57) ABSTRACT

A dose rate-volume histogram can be generated for a target volume. The dose rate-volume histogram can be stored in computer system memory and used to generate a radiation treatment plan. The radiation treatment plan can be used as the basis for treating a patient using a radiation treatment system.

20 Claims, 12 Drawing Sheets

RADIATION TREATMENT BASED ON DOSE RATE

RELATED APPLICATIONS

This application is related to the application with Ser. No. 16/294,693 entitled "Radiation Treatment Planning Based on Dose Rate" by D. Khuntia et al., filed Mar. 6, 2019, and to the application with Ser. No. 16/294,702 entitled "Graphical Display of Dose Rate Information for Radiation Treatment Planning" by D. Khuntia et al., also filed Mar. 6, 2019, both of which are incorporated by reference in their entirety.

BACKGROUND

The use of radiation therapy to treat cancer is well known. Typically, radiation therapy involves directing a beam of high energy proton, photon, ion, or electron radiation ("therapeutic radiation") into a target or target volume (e.g., a volume that includes a tumor or lesion).

Before a patient is treated with radiation, a treatment plan specific to that patient is developed. The plan defines various aspects of the therapy using simulations and optimizations based on past experiences. In general, the purpose of the treatment plan is to deliver sufficient radiation to the unhealthy tissue while minimizing exposure of surrounding healthy tissue to the radiation.

The planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find the one plan that is best suited to achieving the desired outcome.

A recent radiobiology study has demonstrated the effectiveness of delivering an entire, relatively high therapeutic radiation dose to a target within a single, short period of time. For example, each beam can deliver at least four grays (Gy) in less than one second, and may deliver as much as 20 Gy to 50 Gy or as much as 100 Gy or more in less than one second. This type of treatment is referred to generally herein as FLASH radiation therapy (FLASH RT).

Evidence to date suggests that FLASH RT advantageously spares normal, healthy tissue from damage when that tissue is exposed to a high radiation dose for only a very short period of time. FLASH RT thus introduces important constraints that are not considered in or achieved with conventional radiation treatment planning.

SUMMARY

In radiation therapy techniques in which the intensity of the particle beam is either constant or modulated across the field of delivery, such as in intensity modulated radiation therapy (IMRT) and intensity modulated particle therapy (IMPT), beam intensity is varied across each treatment region (target volume) in a patient. Depending on the treatment modality, the degrees of freedom available for intensity modulation include beam shaping (collimation), beam weighting (spot scanning), and angle of incidence (which may be referred to as beam geometry). These degrees of freedom lead to an effectively infinite number of potential treatment plans, and therefore consistently and efficiently generating and evaluating high-quality treatment plans is beyond the capability of a human and relies on the use of a computer system, particularly considering the time constraints associated with the use of radiation therapy to treat ailments like cancer, as well as the large number of patients that are undergoing or need to undergo radiation therapy during any given time period.

Embodiments according to the present invention provide an improved method of radiation treatment planning, and improved radiation treatment based on such planning, for FLASH radiation therapy (FLASH RT).

In embodiments, a dose rate-volume histogram (different from a dose-volume histogram) is generated for a target volume. The dose rate-volume histogram indicates dose rates and percentages of the target volume that receive the dose rates. The dose rate-volume histogram can be stored in computer system memory and used to generate a radiation treatment plan. Values of parameters that can have an effect on dose rate can be adjusted until the dose rate-volume histogram satisfies objectives associated with the radiation treatment plan.

In embodiments, the parameters include a number of irradiations of the target volume, a duration of each of the irradiations, and a dose deposited in each of the irradiations. In an embodiment, the parameters also include directions of beams to be directed into the target volume, and beam energies for each of the beams. In an embodiment, the parameters also include a period of time during which the irradiations are applied (e.g., the irradiations are intermittently applied over a period of time, such as an hour), and an interval of time between each of the periods of irradiations (e.g., each hour-long period is separated by a day).

In embodiments, an irradiation time-volume histogram (also different from a dose-volume histogram) is generated for the target volume. The irradiation time-volume histogram indicates irradiation times (durations) and percentages of the target volume that are irradiated for those amounts of time. The irradiation time-volume histogram can be stored in computer system memory and used to generate a radiation treatment plan. Values of parameters that can have an effect on irradiation time can be adjusted until the irradiation time-volume histogram satisfies objectives associated with the radiation treatment plan.

Both a dose rate-volume histogram and an irradiation time-volume histogram, or only a dose rate-volume histogram, or only an irradiation time-volume histogram, can be generated, evaluated, and used to generate a radiation treatment plan, with or without a dose-volume histogram.

In embodiments, the radiation treatment plan that is based on dose rate as just described is used as the basis for treating a patient using a radiation treatment system.

Embodiments according to the invention improve radiation treatment planning and the treatment itself by expanding FLASH RT to a wider variety of treatment platforms and target sites (e.g., tumors). Treatment plans generated as described herein are superior for sparing healthy tissue from radiation in comparison to conventional techniques for FLASH dose rates by optimizing the balance between the dose rate delivered to unhealthy tissue (e.g., a tumor) in a target volume and the dose rate delivered to surrounding healthy tissue. When used with FLASH dose rates, management of patient motion is simplified because the doses are applied in a short period of time (e.g., less than a second). Treatment planning, while still a complex task, is improved relative to conventional treatment planning.

In summary, embodiments according to this disclosure pertain to generating and implementing a treatment plan that is the most effective (relative to other plans) and with the least (or most acceptable) side effects (e.g., a lower dose rate outside of the region being treated). Thus, embodiments according to the invention improve the field of radiation treatment planning specifically and the field of radiation therapy in general. Embodiments according to the invention allow more effective treatment plans to be generated quickly. Also, embodiments according to the invention help improve the functioning of computers because, for example, by reducing the complexity of generating treatment plans, fewer computational resources are needed and consumed, meaning also that computer resources are freed up to perform other tasks.

In addition to radiation techniques such as IMRT and IMPT, embodiments according to the invention can be used in spatially fractionated radiation therapy including high-dose spatially fractionated grid radiation therapy and microbeam radiation therapy.

These and other objects and advantages of embodiments according to the present invention will be recognized by one skilled in the art after having read the following detailed description, which are illustrated in the various drawing figures.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Figure 1:
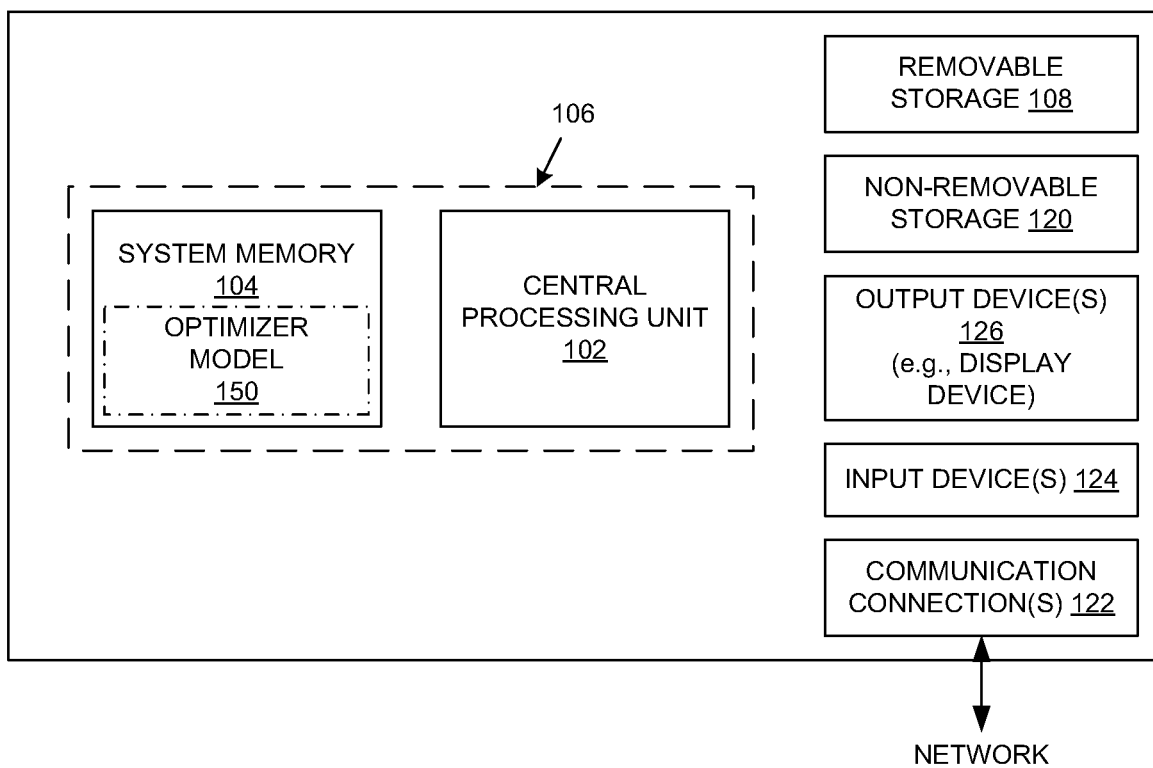
FIG. 1 is a block diagram of an example of a computer system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "generating," "representing," "applying," "indicating," "storing," "using," "adjusting," "including," "computing," "controlling," "directing," "monitoring," or the like, refer to actions and processes (e.g., the flowcharts of FIGS. 8, 10, 11, and 12) of a computer system or similar electronic computing device or processor (e.g., the computer system 100 of FIG. 1). The computer system or similar electronic computing device manipulates and transforms data represented as physical (electronic) quantities within the computer system memories, registers or other such information storage, transmission or display devices. Terms such as "dose" or "dose rate" or "fluence" generally refer to a dose value or dose rate value or fluence value, respectively; the use of such terms will be clear from the context of the surrounding discussion.

Portions of the detailed description that follows are presented and discussed in terms of methods. Although steps and sequencing thereof are disclosed in figures herein (e.g., FIGS. 8, 10, 11, and 12) describing the operations of those methods, such steps and sequencing are examples only. Embodiments are well suited to performing various other steps or variations of the steps recited in the flowcharts of the figures herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 shows a block diagram of an example of a computer system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Output device(s) 126 such as a display device, speakers, printer, etc., are also included.

In the example of FIG. 1, the memory 104 includes computer-readable instructions, data structures, program modules, and the like associated with an "optimizer" model 150. However, the optimizer model 150 may instead reside in any one of the computer storage media used by the system 100, or may be distributed over some combination of the computer storage media, or may be distributed over some combination of networked computers. The functionality of the optimizer model 150 is described below.

Figure 2:
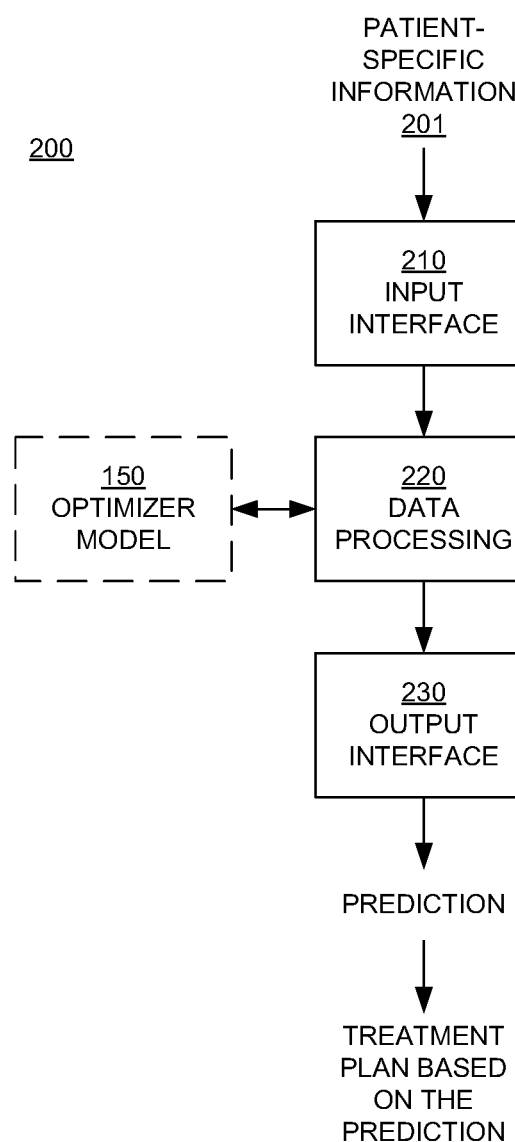
FIG. 2 is a block diagram illustrating an example of an automated radiation therapy treatment planning system in embodiments according to the present invention.

FIG. 2 is a block diagram illustrating an example of an automated radiation therapy treatment planning system 200 in embodiments according to the present invention. The system 200 includes an input interface 210 to receive patient-specific information (data) 201, a data processing component 220 that implements the optimizer model 150, and an output interface 230. The system 200 in whole or in part may be implemented as a software program, hardware logic, or a combination thereof on/using the computer system 100 (FIG. 1).

In the example of FIG. 2, the patient-specific information is provided to and processed by the optimizer model 150. The optimizer model 150 yields a prediction result. A treatment plan based on the prediction result can then be generated.

Figure 3:
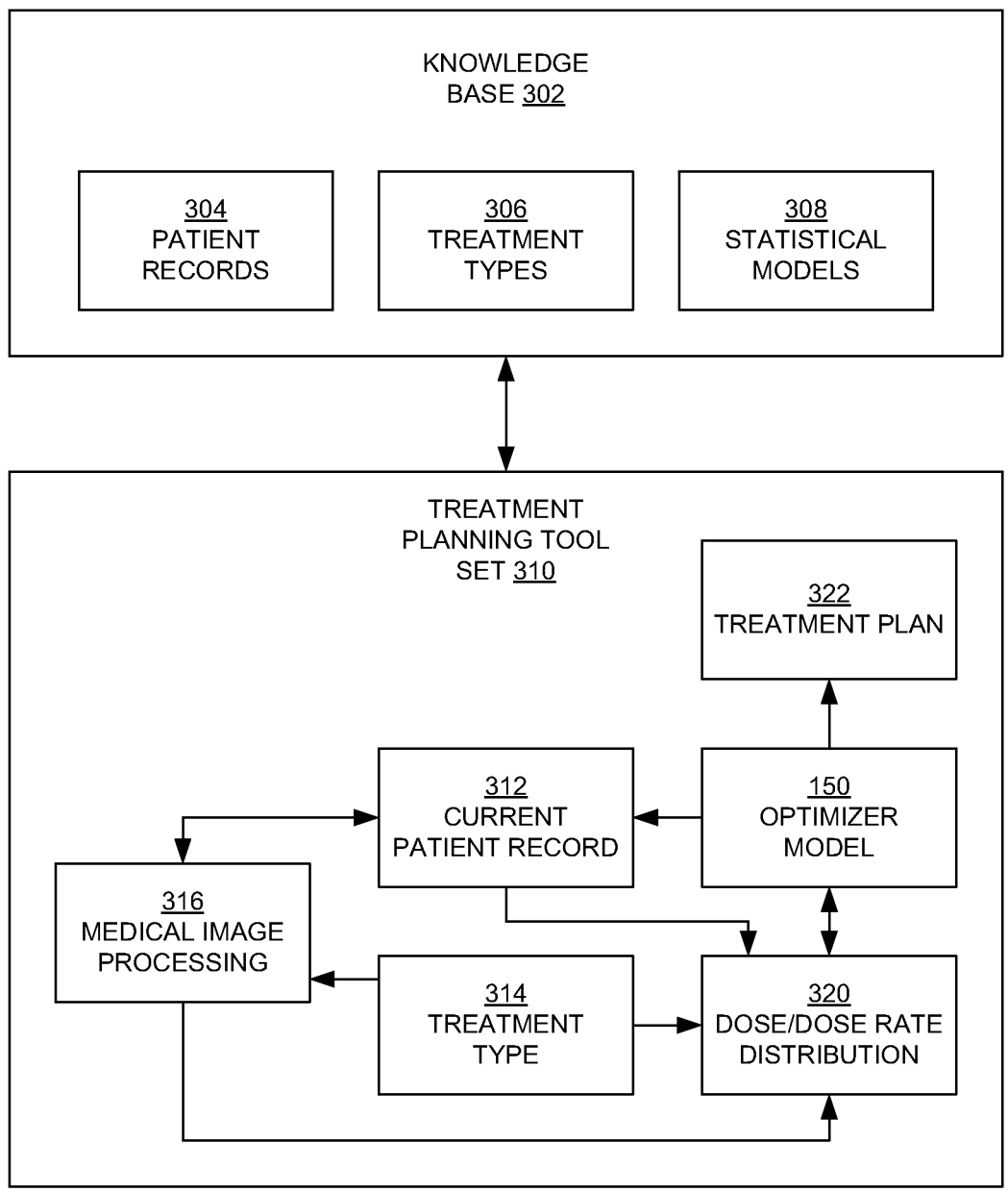
FIG. 3 illustrates a knowledge-based planning system in embodiments according to the present invention.

FIG. 3 illustrates a knowledge-based planning system 300 in embodiments according to the present invention. In the example of FIG. 3, the system 300 includes a knowledge base 302 and a treatment planning tool set 310. The knowledge base 302 includes patient records 304 (e.g., radiation treatment plans), treatment types 306, and statistical models 308. The treatment planning tool set 310 in the example of FIG. 3 includes a current patient record 312, a treatment type 314, a medical image processing module 316, the optimizer model (module) 150, a dose distribution module 320, and a final radiation treatment plan 322.

The treatment planning tool set 310 searches through the knowledge base 302 (through the patient records 304) for prior patient records that are similar to the current patient record 312. The statistical models 308 can be used to compare the predicted results for the current patient record 312 to a statistical patient. Using the current patient record 312, a selected treatment type 306, and selected statistical models 308, the tool set 310 generates a radiation treatment plan 322.

More specifically, based on past clinical experience, when a patient presents with a particular diagnosis, stage, age, weight, sex, co-morbidities, etc., there can be a treatment type that is used most often. By selecting the treatment type that the planner has used in the past for similar patients, a first-step treatment type 314 can be chosen. Patient outcomes, which can include normal tissue complication probability as a function of dose rate and patient-specific treatment-type outcomes (e.g., local recurrent failure, and overall survival as a function of a dose rate-volume histogram (FIG. 7A) and/or an irradiation time-volume histogram (FIG. 7D)), can be included in the treatment planning process. The medical image processing module 316 provides automatic contouring and automatic segmentation of two-dimensional cross-sectional slides (e.g., from any imaging modality such as, but not limited to, computed tomography (CT), positron emission tomography-CT, magnetic resonance imaging, and ultrasound) to form a three-dimensional (3D) image using the medical images in the current patient record 312. Dose distribution maps and dose rate distribution maps are calculated by the dose and dose rate distribution module 320, which may utilize the optimizer model 150.

In embodiments according to the present invention, the optimizer model 150 uses a dose prediction model to provide, for example, a 3D dose distribution, fluences, and dose rates, and associated dose-volume histograms and dose rate-volume histograms.

The discussion to follow refers to beams, target volumes, doses, dose rates, and other elements or values. The discussion below is in the context of modeled elements and calculated values in the treatment planning tool set 310 and the optimizer model 150 (FIG. 3), unless otherwise noted or made clear in the discussion.

Figure 4:
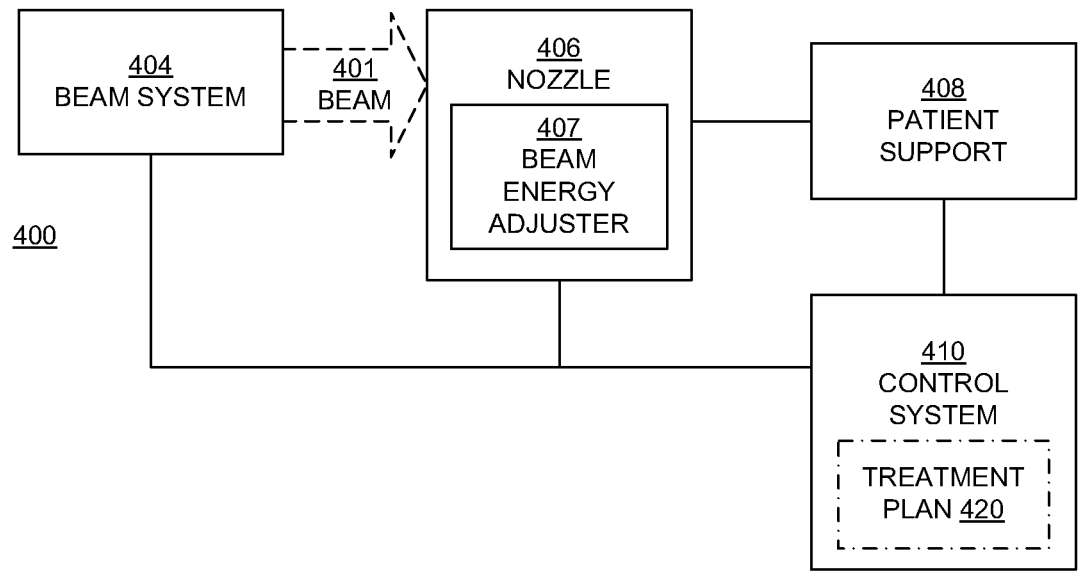
FIG. 4 is a block diagram showing selected components of a radiation therapy system upon which embodiments according to the present invention can be implemented.

FIG. 4 is a block diagram showing selected components of a radiation therapy or treatment system 400 upon which embodiments according to the present invention can be implemented. In the example of FIG. 4, the system 400 includes a beam system 404 and a nozzle 406.

The beam system 404 generates and transports a beam 401. The beam 401 can be a proton beam, electron beam, photon beam, ion beam, or atom nuclei beam (e.g., carbon, helium, and lithium). In embodiments, depending on the type of beam, the beam system 404 includes components that direct (e.g., bend, steer, or guide) the beam system in a direction toward and into a nozzle 406. In embodiments, the radiation therapy system may include one or more multileaf collimators (MLCs); each MLC leaf can be independently moved back-and-forth by the control system 410 to dynamically shape an aperture through which the beam can pass, to block or not block portions of the beam and thereby control beam shape and exposure time. The beam system 404 may also include components that are used to adjust (e.g., reduce) the beam energy entering the nozzle 406.

The nozzle 406 is used to aim or direct the beam toward various locations (a target volume) within an object (e.g., a patient) supported on the patient support device 408 (e.g., a chair or table) in a treatment room. A target volume may be an organ, a portion of an organ (e.g., a volume or region within the organ), a tumor, diseased tissue, or a patient outline. A target volume may include both unhealthy tissue (e.g., a tumor) and healthy tissue.

The nozzle 406 may be mounted on or a part of a gantry that can be moved relative to the patient support device 408, which may also be moveable. In embodiments, the beam system 404 is also mounted on or is a part of the gantry. In another embodiment, the beam system is separate from (but in communication with) the gantry.

The control system 410 receives and implements a prescribed radiation treatment plan. In embodiments, the control system 410 includes a computer system having a processor, memory, an input device (e.g., a keyboard), and perhaps a display as in the example of FIG. 1. The control system 410 can receive data regarding operation of the system 400. The memory of the control system 410 stores a prescribed radiation treatment plan 420 that will be implemented using the system 400. Specifically, the memory of the control system 410 includes computer-readable instructions, data structures, program modules, and the like associated with the prescribed radiation treatment plan 420. The control system 410 can control parameters of the beam system 404, nozzle 406, and patient support device 408, including parameters such as the energy, intensity, direction, size, and/or shape of the beam, according to data it receives and according to the prescribed radiation treatment plan 420.

As noted above, the beam entering the nozzle 406 of FIG. 4 has a specified energy. Thus, in some embodiments according to the present disclosure, the nozzle 406 includes one or more components that affect (e.g., decrease, modulate) the energy of the beam. The term "beam energy adjuster" is used herein as a general term for a component or components that affect the energy of the beam, in order to control the range of the beam (e.g., the extent that the beam penetrates into a target), to control the dose delivered by the beam, and/or to control the depth dose curve of the beam, depending on the type of beam. For example, for a proton beam or an ion beam that has a Bragg peak, the beam energy adjuster can control the location of the Bragg peak in the target volume. In various embodiments, the beam energy adjuster 407 includes a range modulator, a range shifter, or both a range modulator and a range shifter.

In radiation therapy techniques in which the intensity of the particle beam is either constant or modulated across the field of delivery, such as in intensity modulated radiation therapy (IMRT) and intensity modulated particle therapy (IMPT), beam intensity is varied across each treatment region (target volume) in a patient. Depending on the treatment modality, the degrees of freedom available for intensity modulation include beam shaping (collimation), beam weighting (spot scanning), and angle of incidence (which may be referred to as beam geometry). These degrees of freedom lead to an effectively infinite number of potential treatment plans, and therefore consistently and efficiently generating and evaluating high-quality treatment plans is beyond the capability of a human and relies on the use of a computer system, particularly considering the time constraints associated with the use of radiation therapy to treat ailments like cancer, as well as the large number of patients that are undergoing or need to undergo radiation therapy during any given time period.

Figure 5:
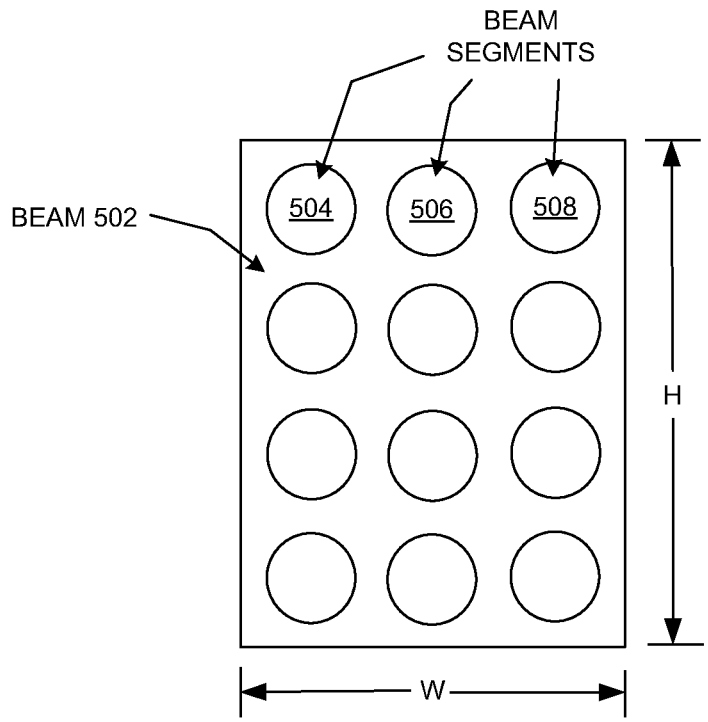
FIG. 5 illustrates a beam's eye view of a beam in embodiments according to the invention.

FIG. 5 illustrates a beam's eye view (BEV) of a beam 502 in embodiments according to the invention. That is, FIG. 5 illustrates a cross-section of a beam. The beam 502 is illustrated as being rectangular in shape having a height H and width W. However, the invention is not so limited, and the beam 502 can have virtually any regular or irregular cross-sectional (e.g., BEV) shape. For example, the shape of the beam 502 can be defined using an MLC that blocks a portion or portions of the beam. Different beams can have different shapes.

In the FIG. 5 embodiment, the beam 502 includes a number of beam segments or beam lets (that also may be referred to as spots) exemplified by beam segments 504, 506, and 508. A maximum energy (e.g., 80 MeV) is specified for the beam 502, and an energy level is defined for each of the beam segments as a percentage or fraction of the maximum energy. In essence, each of the beam segments is weighted in terms of its energy level; some beam segments are weighted to have a higher energy level than other beam segments. By weighting the energy per beam segment, in effect the intensity of each beam segment is also weighted. The defined energy level or intensity can be realized for each beam segment using the beam energy adjuster 407 of FIG. 4.

Each beam segment can deliver a relatively high dose rate (a relatively high dose in a relatively short period of time). For example, each beam segment can deliver at least four grays (Gy) in less than one second, and may deliver as much as 20 Gy to 50 Gy or 100 Gy or more in less than one second.

In operation, in embodiments, the beam segments are delivered sequentially. For example, the beam segment 504 of FIG. 5 is delivered to the target volume (turned on) and then turned off, then the beam segment 506 is turned on then off, then the beam segment 508 is turned on then off, and so on. Each beam segment may be turned on for only a fraction of a second (e.g., on the order of milliseconds).

Figure 6A:
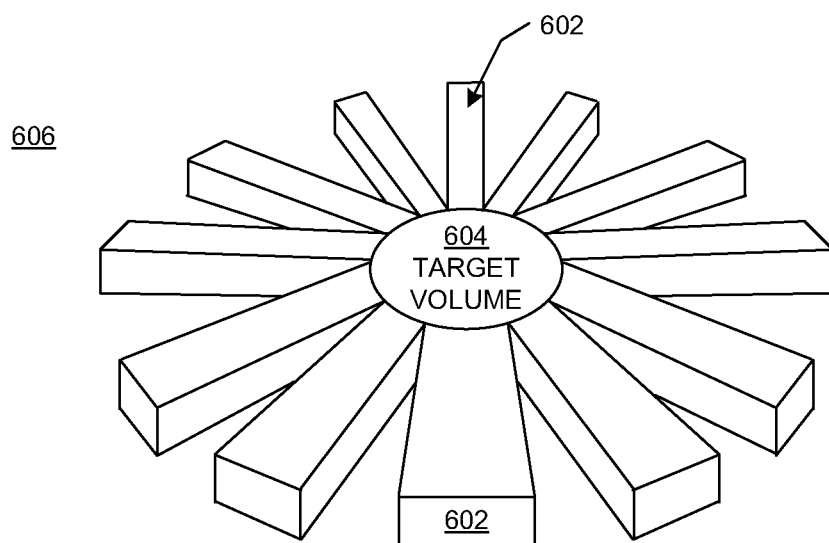
FIG. 6A illustrates a perspective view of an example of a beam geometry in embodiments according to the invention.

FIG. 6A illustrates a perspective view of an example of a beam geometry in embodiments according to the invention. In the example of FIG. 6A, the beams (exemplified by beam 602) are in the same plane. The beams can be proton beams, electron beams, photon beams, ion beams, or atom nuclei beams. Each beam can deliver a relatively high dose rate (a relatively high dose in a relatively short period of time). For example, in embodiments, each beam can deliver doses sufficient for FLASH RT (e.g., at least 4 Gy in less than one second, and as much as 20 Gy to 50 Gy or 100 Gy or more in less than one second). Each beam can include one or more beam segments or beamlets. In this example, the beams' paths overlap only within the target volume 604, and do not overlap outside the target volume in the surrounding tissue 606.

In the example of FIG. 6A, the beam 602 (for example) is illustrated as passing completely through the target volume 604. For beams that have a Bragg peak (e.g., proton beams and ion beams), the ranges of the beams can be controlled so that the beam does not pass completely through the target volume.

Although multiple beams are shown in FIG. 6A, this does not mean that all beams are necessarily delivered at the same time or in overlapping time periods, although they can be. The number of beams delivered at any one time depends on the number of gantries or nozzles in the radiation treatment system (e.g., the radiation treatment system 400 of FIG. 4) and on the treatment plan.

Figure 6B:
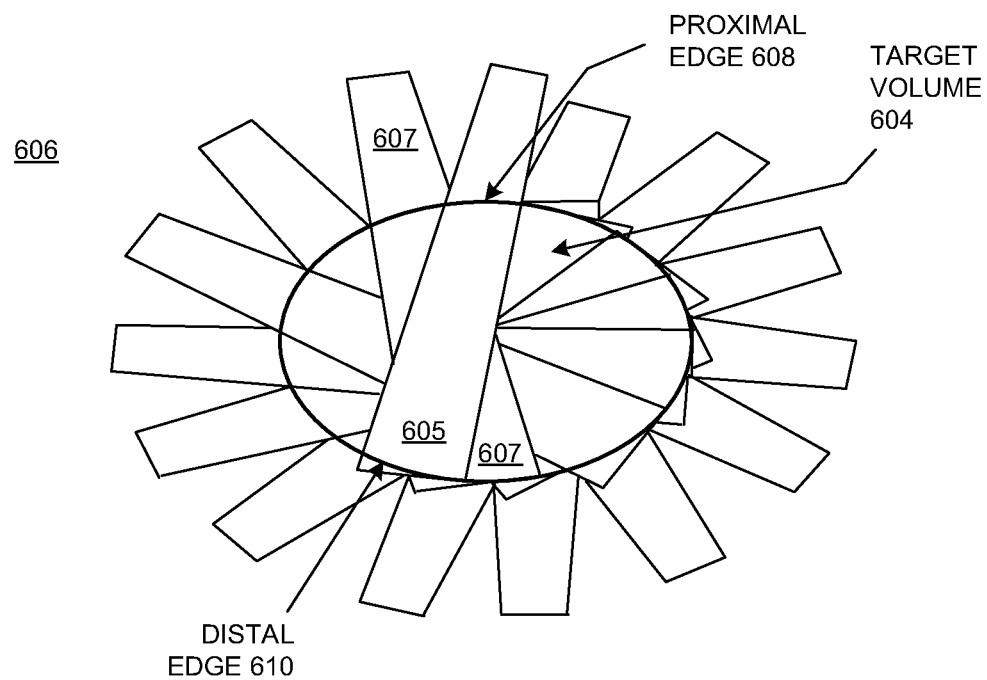
FIG. 6B illustrates a cross-sectional view of an example of a beam geometry in embodiments according to the invention.

FIG. 6B illustrates a cross-sectional view of an example of a beam geometry in embodiments according to the invention. In this example, the beams (exemplified by beams 605 and 607) overlap only within the target volume and are in the same plane. The figure depicts the beams in overlapping fashion to demonstrate that each portion of the target volume 604 receives a dose of radiation. The beams can be proton beams, electron beams, photon beams, ion beams, or atom nuclei beams. In the example of FIG. 6B, the beams are illustrated as not extending beyond the distal edge of the target volume 604 (as would be the case for proton or ion beams, for example); however, the invention is not so limited. Each beam can deliver a relatively high dose in a relatively short period of time. For example, each beam can deliver dose rates sufficient for FLASH RT.

Figure 6C:
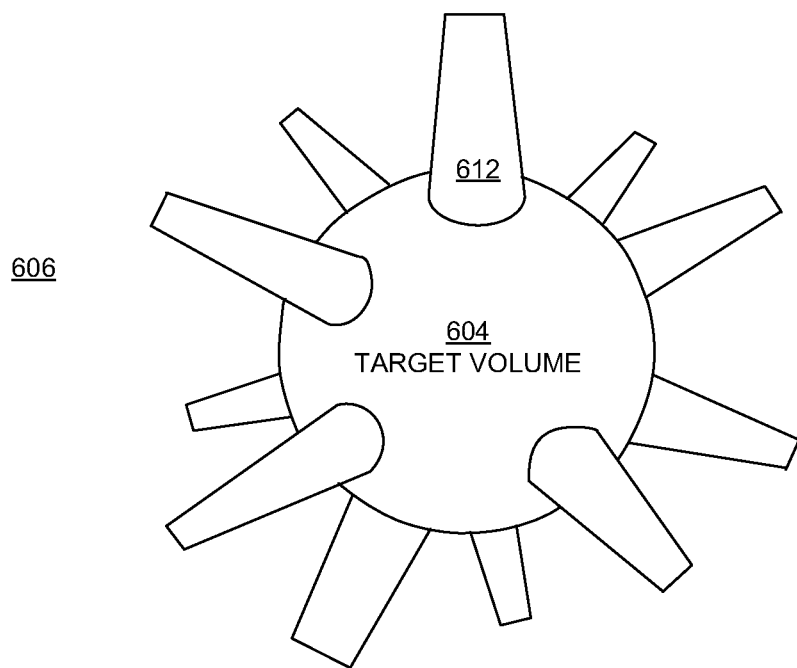
FIG. 6C illustrates a perspective view of an example of a beam geometry in embodiments according to the invention.

FIG. 6C illustrates a perspective view of an example of a beam geometry in embodiments according to the invention. In the example of FIG. 6C, the beams (exemplified by beam 612) are in different planes. Each beam can include one or more beam segments or beamlets. In this example, the beams' paths overlap only within the target volume 604, and do not overlap outside the target volume in the surrounding tissue 606. Although multiple beams are shown in the figure, all beams are not necessarily delivered at the same time or in overlapping time periods as mentioned above. The beams can be proton beams, electron beams, photon beams, ion beams, or atom nuclei beams. Each beam can deliver a relatively high dose in a relatively short period of time. For example, each beam can deliver dose rates sufficient for FLASH RT.

Figure 6D:
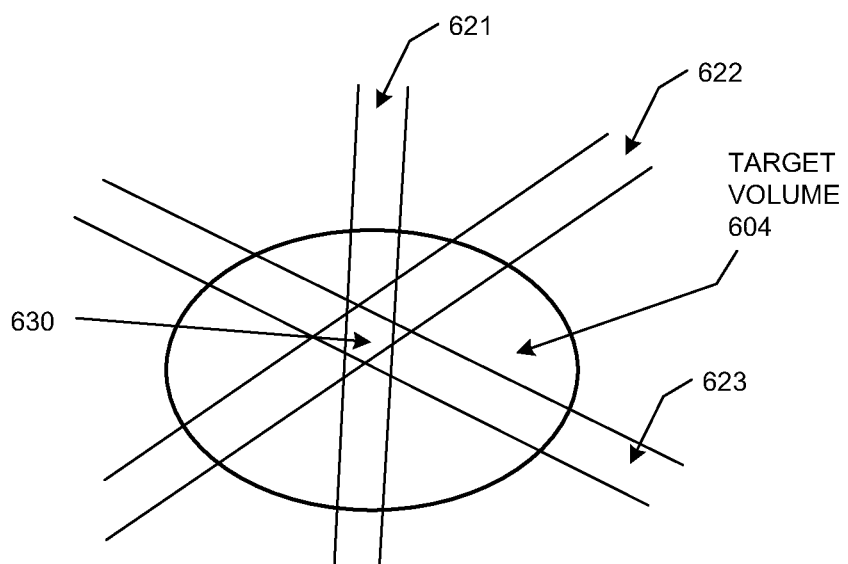
FIG. 6D illustrates a cross-sectional view of an example of a beam geometry in embodiments according to the invention.

FIG. 6D illustrates a cross-sectional view of an example of a beam geometry in embodiments according to the invention. In this example, the beams (exemplified by beams 621, 622, and 623) overlap only within the target volume and are in the same plane. While three beams are illustrated, the invention is not so limited. As described herein, each beam can include one or more beam segments or beamlets. In this example, the beams' paths overlap only within the target volume 604, and do not overlap outside the target in the surrounding tissue 606. Although multiple beams are shown in the figure, all beams are not necessarily delivered at the same time or in overlapping time periods as mentioned above. The beams can be proton beams, electron beams, photon beams, ion beams, or atom nuclei beams. Each beam can deliver a relatively high dose in a relatively short period of time. For example, each beam can deliver dose rates sufficient for FLASH RT.

In the example of FIG. 6D, the beams 621, 622, and 623 intersect at the sub-volume 630, other sub-volumes in the target volume 604 receive doses from two of the beams, other sub-volumes in the target volume receive doses from only one of the beams, and yet other sub-volumes do not receive a dose. The directions and/or numbers of beam can be varied over a number of treatment sessions (that is, fractionated in time) so that a uniform dose is delivered across the target.

In embodiments according to the present invention, a dose rate-volume histogram (which is different from, but may be used with, a dose-volume histogram) is generated for a target volume. The dose rate-volume histogram can be generated based on a proposed radiation treatment plan. The dose rate-volume histogram can be stored in computer system memory and used to generate a final radiation treatment plan that will be used to treat a patient. Values of parameters that can have an effect on dose rate can be adjusted until the dose rate-volume histogram satisfies objectives of or associated with treatment of the patient.

Figure 7A:
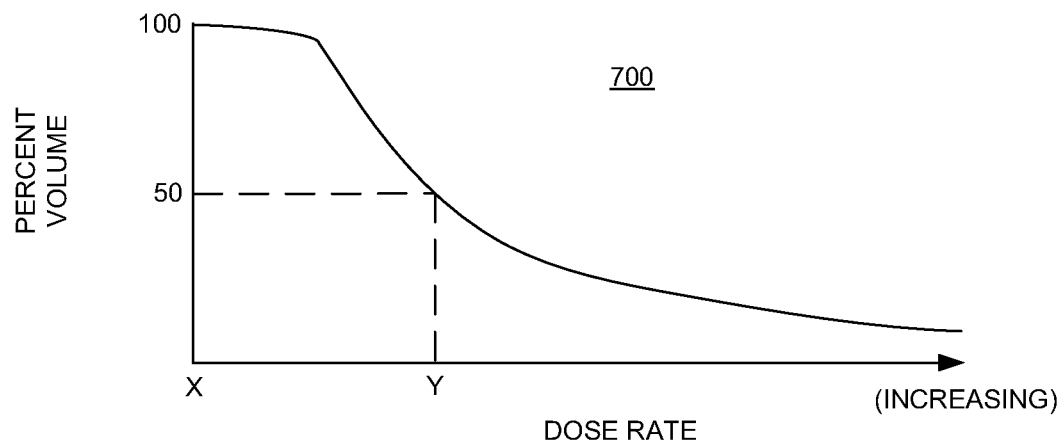
FIGS. 7A and 7B illustrate examples of dose rate-volume histograms in an embodiment according to the present invention.

FIG. 7A illustrates an example of a dose rate-volume histogram 700 in an embodiment according to the present invention. The dose rate-volume histogram plots a cumulative dose rate-to-target volume frequency distribution that summarizes the simulated dose rate distribution within a target volume of interest (e.g., the target volume 604 of FIGS. 6A-6D) that would result from a proposed radiation treatment plan. The simulated dose rate distribution can be determined using the optimizer model 150 of FIG. 1. The dose rate-volume histogram indicates dose rates and percentages of the target volume that receive the dose rates. For example, as shown in FIG. 7A, 100 percent of the target volume receives a dose rate of X, 50 percent of the target volume receives a dose rate of Y, and so on.

Figure 7B:
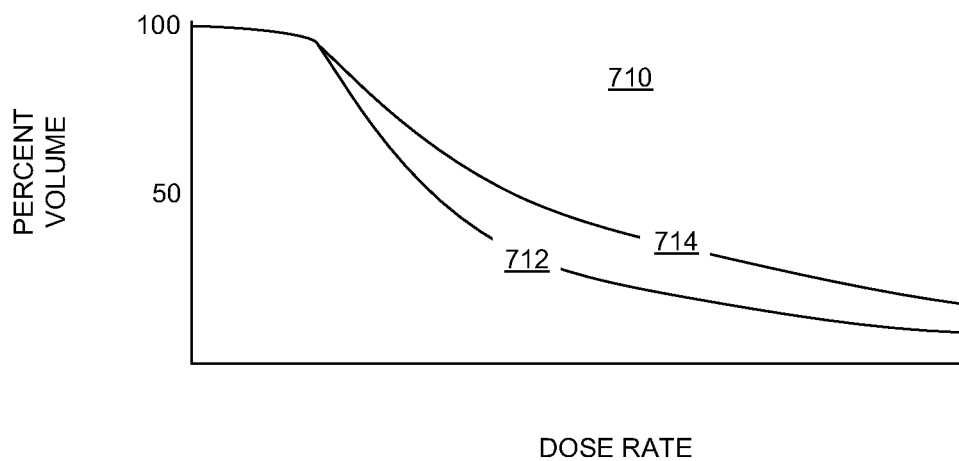
Figure 7C:
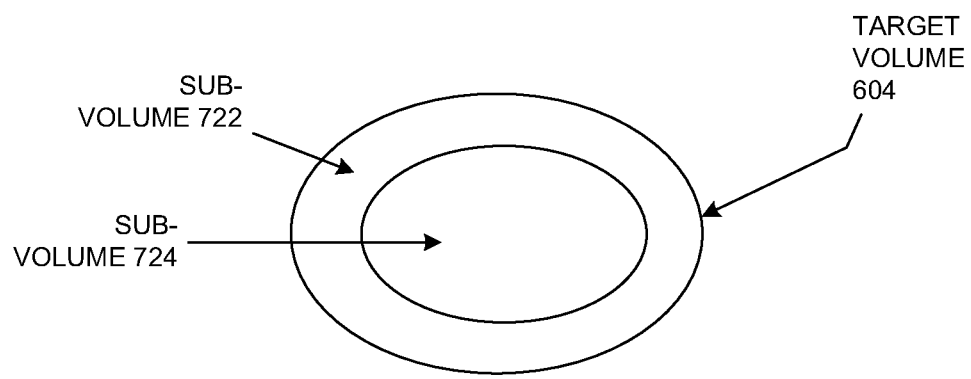
FIG. 7C illustrates sub-volumes in a target volume in an embodiment according to the present invention.

The target volume 604 may include different organs, for example, or it may include both healthy tissue and unhealthy tissue (e.g., a tumor). Accordingly, with reference to FIGS. 7B and 7C, the dose rate-volume histogram 710 includes multiple curves 712 and 714, showing the simulated dose rate distribution for a first sub-volume 722 of the target volume (e.g., for one organ, or for the healthy tissue) and the simulated dose rate distribution for a second sub-volume 724 (e.g., for a second organ, or for the unhealthy tissue), respectively. More than two simulated dose rate distributions can be included in a dose rate-volume histogram.

The target volume 604 may be divided (virtually) into a number of voxels. A sub-volume can include a single voxel or multiple voxels.

In embodiments according to the present invention, an irradiation time-volume histogram (which is different from, but may be used with, a dose-volume histogram and/or a dose rate-volume histogram) is generated for the target volume. The irradiation time-volume histogram can be stored in computer system memory and used to generate a radiation treatment plan, in combination with or in lieu of a dose-volume histogram and/or a dose rate-volume histogram.

Figure 7D:
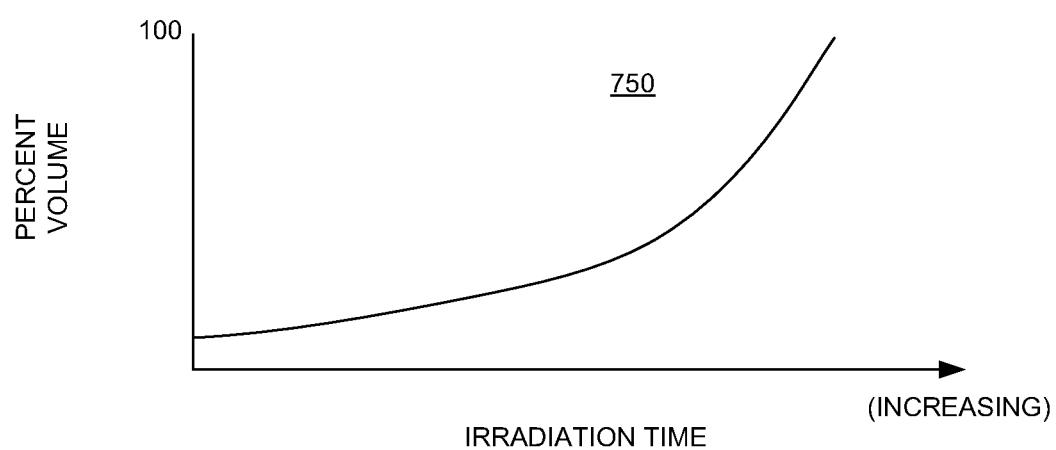
FIG. 7D illustrates an example of an irradiation time-volume histogram in an embodiment according to the present invention.

FIG. 7D illustrates an example of an irradiation time-volume histogram 750 in an embodiment according to the present invention. The irradiation time-volume histogram plots a cumulative irradiation time-to-target volume frequency distribution that summarizes the simulated irradiation time distribution within a target volume of interest (e.g. the target volume 604 of FIGS. 6A-6D) that would result from a proposed radiation treatment plan. The simulated irradiation time distribution can be determined using the optimizer model 150 of FIG. 1. The irradiation time-volume histogram indicates irradiation times (lengths of times) and percentages of the target volume that are irradiated for those lengths of time.

Figure 8:
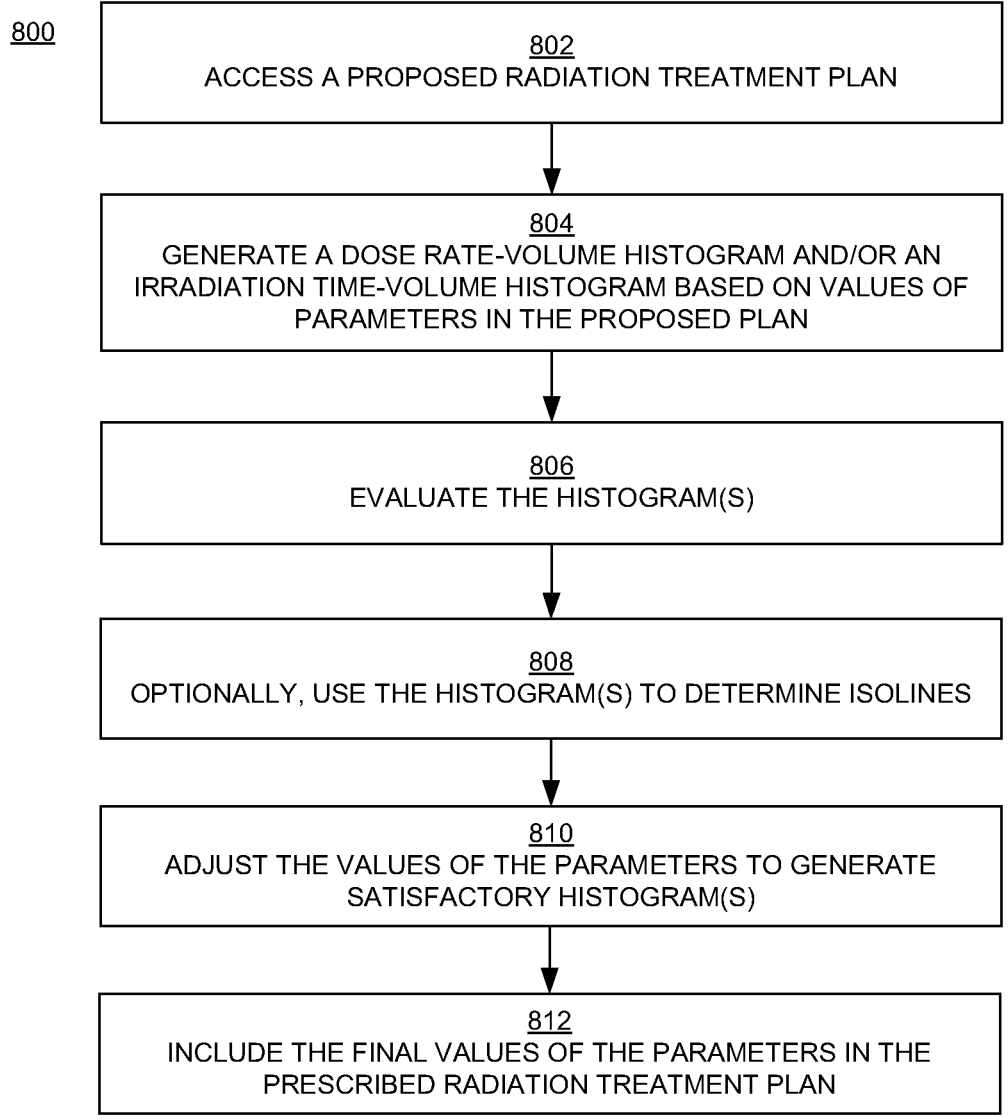
FIG. 8 is a flowchart of an example of computer-implemented operations for radiation treatment planning in embodiments according to the present invention.

FIG. 8 is a flowchart 800 of an example of computer-implemented operations for radiation treatment planning including generating a dose rate-volume histogram or an irradiation time-volume histogram in embodiments according to the present invention. The flowchart 800 can be implemented as computer-executable instructions (e.g., the optimizer model 150 of FIG. 1) residing on some form of computer-readable storage medium (e.g., in memory of the computer system 100 of FIG. 1).

In block 802 of FIG. 8, a proposed radiation treatment plan is defined (e.g., using the optimizer model 150 of FIGS. 1 and 2), stored in a computer system memory, and accessed. The proposed radiation treatment plan includes values of parameters that can affect dose rate, as well as other parameters. The parameters that can affect dose rate include, but are not limited to, a number of irradiations of the target volume, a duration of each of the irradiations (irradiation times), and a dose deposited in each of the irradiations. The parameters may also include directions of beams to be directed into the target volume, and beam energies for each of the beams. The parameters may also include a period of time during which the irradiations are applied (e.g., a number of irradiations are applied over a period of time such as an hour, with each irradiation in the period of time separated from the next by another period of time) and an interval of time between each period of irradiations (e.g., each hour-long period is separated from the next by a day). If the target volume is divided into sub-volumes or voxels, then the values of the parameters can be on a per-sub-volume or per-voxel basis (e.g., a value per sub-volume or voxel).

Appropriate dose threshold curve(s) (e.g., normal tissue sparing dose versus dose rate or irradiation time) can be utilized in the optimization model 150 (FIG. 3) to establish dose limits for radiation treatment planning. For example, the appropriate (e.g., tissue-dependent) dose threshold curve can be used to determine beam directions (gantry angles) and beam segment weights (FIG. 7A). That is, parameters that affect dose can be adjusted during radiation treatment planning so that the limits in the dose threshold curve are satisfied. The dose threshold curves can be tissue-dependent. For instance, the dose threshold curve for the lungs may be different from that for the brain.

Dose limits can include, but are not limited to: a maximum limit on irradiation time for each sub-volume (voxel) in the target (e.g., for each voxel of target tissue, treatment time less than x1 seconds); a maximum limit on irradiation time for each sub-volume (voxel) outside the target (e.g., for each voxel of normal tissue, treatment time less than x2 seconds); x1 and x2 may be the same or different); a minimum limit on dose rate for each sub-volume (voxel) in the target (e.g., for each voxel of target tissue, dose rate greater than y1 Gy/sec); and a minimum limit on dose rate for each sub-volume (voxel) outside the target (e.g., for each voxel of normal tissue, dose rate greater than y2 Gy/sec; y1 and y2 may be the same or different). In general, the limits are intended to minimize the amount of time that normal tissue is irradiated.

In block 804, in an embodiment, a dose rate-volume histogram is generated based on the values of the parameters in the proposed radiation treatment plan. A dose rate can be determined per sub-volume or voxel. The dose rate is the dose deposited in each irradiation divided by the sum of the durations of the irradiation, times the number of irradiations (e.g., number of fractions). The dose rate can be determined and recorded using a fine time index (e.g., time increments on the order of a millisecond); that is, for example, the dose to each sub-volume or voxel can be recorded for time increments on the order of per-millisecond per beam and per fraction. The dose rate is cumulative. The cumulative dose rate for some portions (e.g., sub-volumes or voxels) of the target volume may be higher than other portions, depending on the beam directions and energies, for example. The dose rate per sub-volume or voxel can be calculated to include ray tracing (and Monte Carlo-like simulations), where each beam particle is tracked to determine the primary, secondary, etc., scatters for each particle to get a realistic voxel-based or sub-volume-based dose rate over the course of each irradiation.

In an embodiment, an irradiation time-volume histogram is generated. An irradiation time-volume histogram can be generated essentially in the same manner as that just described for generating a dose rate-volume histogram. Both a dose rate-volume histogram and an irradiation time-volume histogram, or only a dose rate-volume histogram, or only an irradiation time-volume histogram, can be generated, in addition to or in lieu of a dose-volume histogram.

In block 806, the dose rate-volume histogram and/or the irradiation time-volume histogram can be evaluated by determining whether or not objectives (e.g., clinical goals) that are specified for treatment of a patient are satisfied by the proposed radiation treatment plan. The clinical goals or objectives may be expressed in terms of a set of quality metrics, such as target homogeneity, critical organ sparing, and the like, with respective target values for the metrics. Another way to evaluate the dose rate-volume histogram and/or the irradiation time-volume histogram is a knowledge-based approach that incorporates and reflects present best practices gathered from multiple previous, similar treatments of other patients. Yet another way to assist the planner is to use a multi-criteria optimization (MCO) approach for treatment planning. Pareto surface navigation is an MCO technique that facilitates exploration of the tradeoffs between clinical goals. For a given set of clinical goals, a treatment plan is considered to be Pareto optimal if it satisfies the goals and none of the metrics can be improved without worsening at least one of the other metrics.

As mentioned above, for FLASH RT, dose rates of at least 4 Gy in less than one second, and as much as 20 Gy to 50 Gy or 100 Gy or more in less than one second, may be used. Thus, another way to evaluate a dose rate-volume histogram is to define a dose rate threshold value (e.g., a minimum dose rate) based on the FLASH RT dose rates, and to also specify a target volume percentage threshold value for dose rate. A dose rate-volume histogram can be evaluated by determining whether the percentage of the target volume that receives a dose rate above the dose rate threshold value satisfies the percentage threshold value. For example, a dose-rate volume histogram may be considered to be satisfactory if 80 percent of the target volume (specifically, the portion of the target volume that includes the unhealthy tissue) receives a dose rate of at least 50 Gy per second.

Another way to evaluate an irradiation time-volume histogram is to define an irradiation time threshold value or values (e.g., a maximum limit on irradiation time for each sub-volume or voxel inside the target volume and/or a maximum limit on irradiation time for each sub-volume or voxel outside the target volume), and to also specify a target volume percentage threshold value or values for irradiation time inside and/or outside the target volume. An irradiation time-volume histogram can be evaluated by determining whether the percentage of the tissue inside the target volume that is irradiated for less than the corresponding irradiation time threshold value satisfies the corresponding percentage threshold value, and/or by similarly determining whether the percentage of the tissue outside the target volume that is irradiated for less than the corresponding irradiation time threshold value satisfies the corresponding percentage threshold value.

Figure 9:
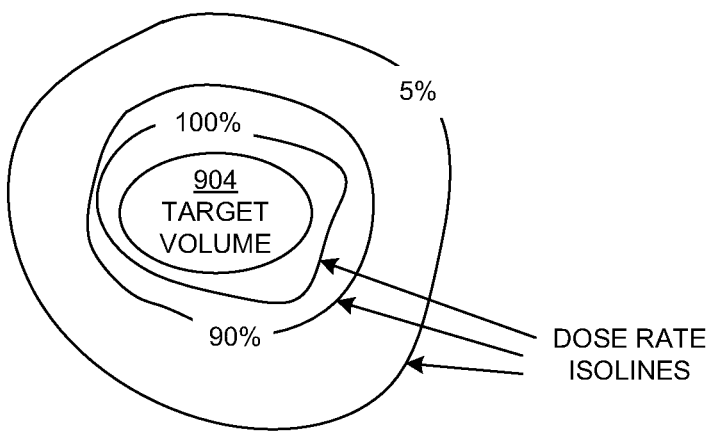
FIG. 9 illustrates an example of dose rate isolines relative to a target volume in embodiments according to the present invention.

In block 808, in an embodiment, the information in the dose rate-volume histogram is used to determine and represent isolines of dose rate relative to a target volume 904 (e.g., a tumor) that includes or is surrounded by other (e.g., healthy) tissue, as shown in the example of FIG. 9. In that example, the 100 percent, 90 percent, and five percent dose rate isolines are shown. FIG. 9 is illustrated in two dimensions, showing either a top down view of the target volume or one cross-sectional slice of the target volume. However, the target volume and isolines can be represented in three dimensions and displayed.

Isolines of irradiation time relative to a target volume can be similarly determined and represented.

In block 810 of FIG. 8, some or all of the parameter values for the proposed radiation treatment plan can be iteratively adjusted to generate different dose rate-volume histograms and/or the irradiation time-volume histograms, to determine a final set of parameter values that produce a histogram (or histograms) that results in a prescribed (final) radiation treatment plan that best satisfies the objectives (clinical goals) for treatment of the patient or that satisfies the threshold values described above.

In block 812, the final set of parameter values is then included in the prescribed radiation treatment plan used to treat the patient.

Generally speaking, embodiments according to the invention optimize a radiation treatment plan based on dose rate and/or irradiation time. This is not to say that treatment plan optimization is based solely on dose rate and/or irradiation time. For example, a dose-volume histogram can be used in conjunction with a dose rate-volume histogram and/or irradiation time-volume histogram when developing a radiation treatment plan.

Figure 10:
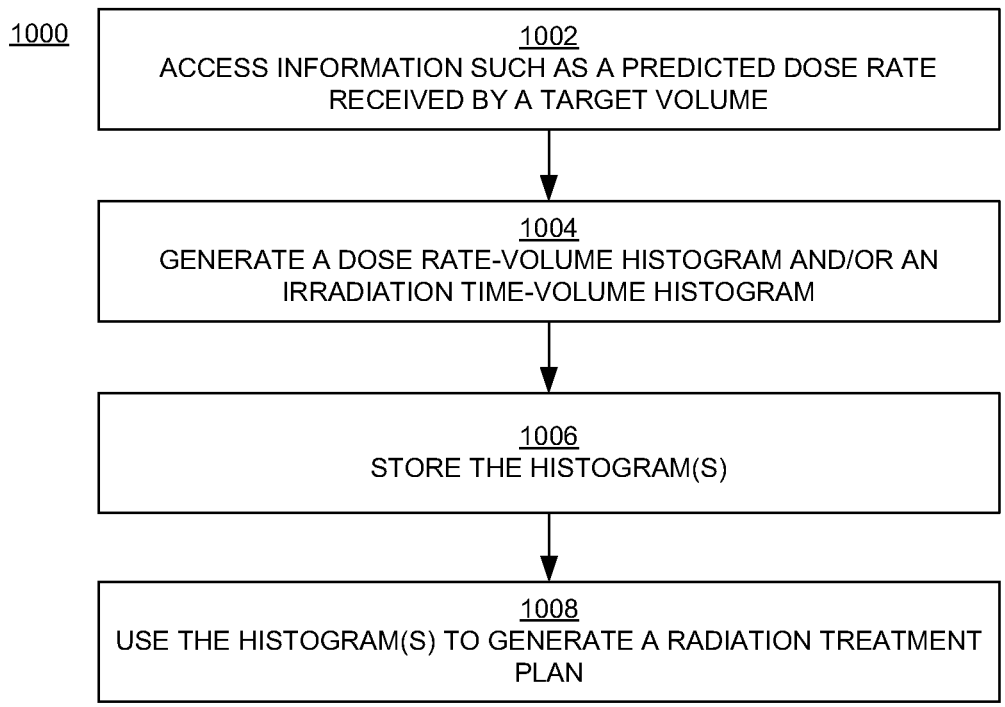
FIG. 10 is a flowchart of an example of computer-implemented operations for radiation treatment planning in embodiments according to the present invention.

FIG. 10 is a flowchart 1000 of an example of computer-implemented operations for radiation treatment planning including generating a dose rate-volume histogram in embodiments according to the present invention. The flowchart 1000 can be implemented as computer-executable instructions (e.g., the optimizer model 150 of FIG. 1) residing on some form of computer-readable storage medium (e.g., memory of the computer system 100 of FIG. 1).

In block 1002 of FIG. 10, information in computer system memory is accessed. The information includes a dose rate received by a target volume per sub-volume or voxel, determined using a dose prediction model implemented with the optimizer model 150 (FIG. 1). The information also can include irradiation time (duration) per sub-volume or voxel.

In block 1004 of FIG. 10, a dose rate-volume histogram and/or an irradiation time-volume histogram are/is generated for the target volume, as previously described herein (e.g., with reference to FIG. 8).

In block 1006 of FIG. 10, histograms that are generated are stored in computer system memory.

In block 1008, the dose rate-volume histogram and/or the irradiation time-volume histogram are/is used to generate a radiation treatment plan for treating the target volume.

Figure 11:
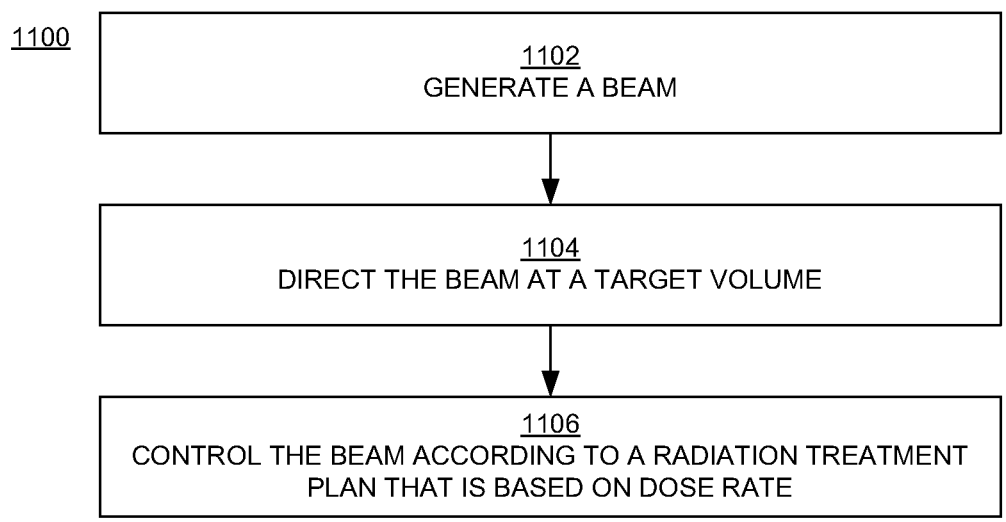
FIGS. 11 and 12 are flowcharts of examples of operations using a radiation treatment system in embodiments according to the present invention.
Figure 12:
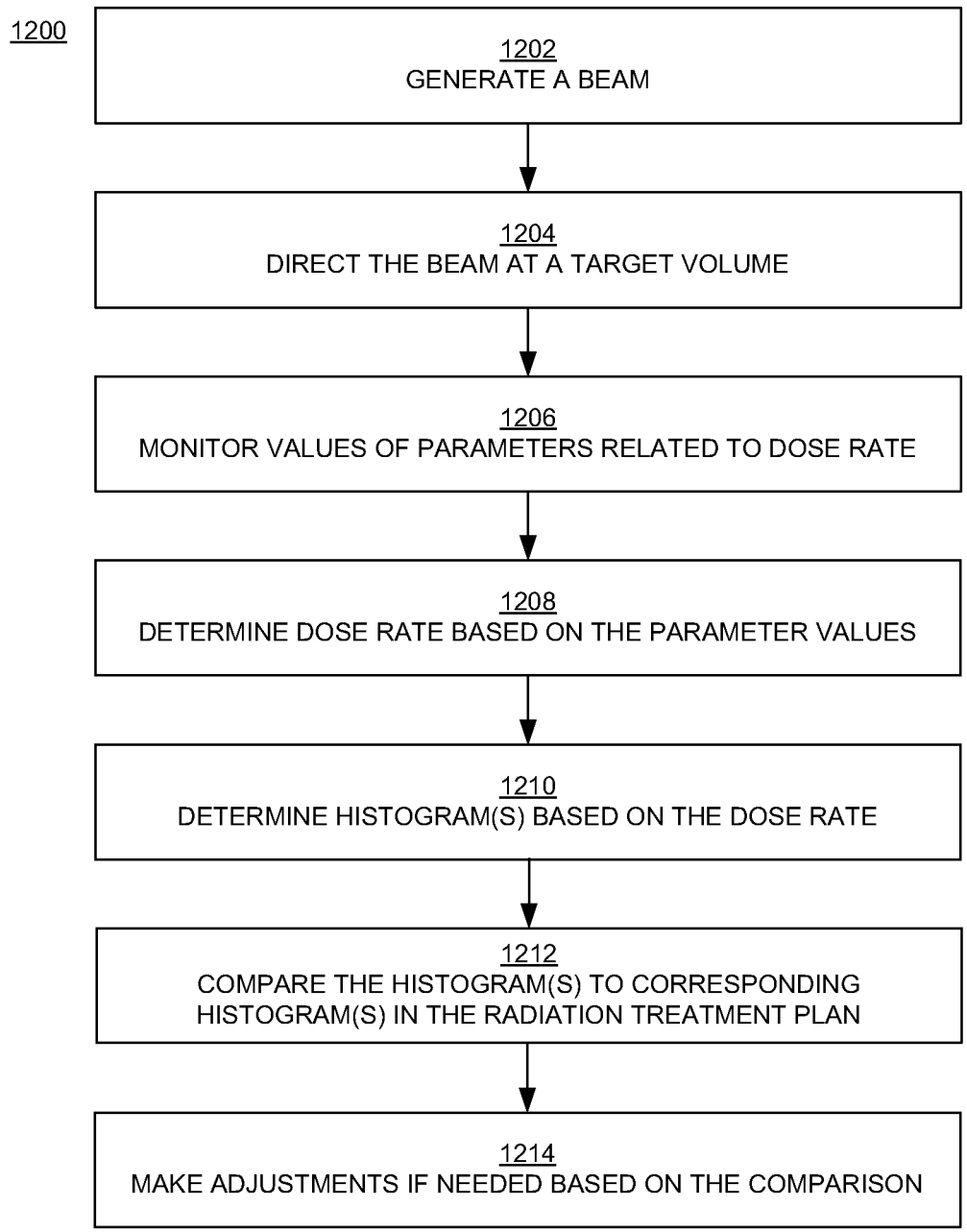

FIGS. 11 and 12 are flowcharts 1100 and 1200, respectively, of examples of operations using a radiation treatment system (e.g., the system 400 of FIG. 4) in embodiments according to the present invention. The flowcharts 1100 and 1200 can be implemented as computer-executable instructions (e.g., the radiation treatment plan 420 of FIG. 4) residing on some form of computer-readable storage medium (e.g., in memory of the control system 410 of FIG. 4).

In block 1102 of FIG. 11, a beam is generated with a beam system (e.g., the beam 401 is generated by the beam system 404 of FIG. 4).

In block 1104 of FIG. 11, the beam is directed at a target volume with a nozzle coupled to the beam system (e.g., the nozzle 406 of FIG. 4).

In block 1106 of FIG. 11, the beam is controlled with a control system (e.g., the control system 410 of FIG. 4) according to a radiation treatment plan stored in the memory of the control system. In an embodiment, the radiation treatment plan includes a dose rate-volume histogram for the target volume as previously described herein. In an embodiment, the radiation treatment plan also includes isolines of dose rates relative to the target volume based on the dose rate-volume histogram as previously described herein. In an embodiment, the radiation treatment plan includes an irradiation time-volume histogram for the target volume as previously described herein.

In block 1202 of FIG. 12, a beam is generated with a beam system (e.g., the beam 401 is generated by the beam system 404 of FIG. 4).

In block 1204 of FIG. 12, the beam is directed at a target volume with a nozzle coupled to the beam system (e.g., the nozzle 406 of FIG. 4).

In block 1206 of FIG. 12, a control system (e.g., the control system 410 of FIG. 4) monitors values of parameters that are related to dose rate, specifically the dose rate to the target volume and, more specifically, the dose rate to each sub-volume of the target volume. Those parameter values include, but are not limited to, a number of irradiations of each sub-volume of the target volume, a duration of each of the irradiations for each sub-volume, and a dose deposited in each sub-volume, that result from the beam being directed into the target volume.

In block 1208 of FIG. 12, a dose rate is determined for each sub-volume using the values of the parameters.

In block 1210, in an embodiment, a dose rate-volume histogram for the target volume is determined using the dose rate for each sub-volume as previously described herein. In an embodiment, an irradiation time-volume histogram for the target volume is determined as previously described herein.

In block 1212, in an embodiment, a comparison is made between the dose rate-volume histogram and/or the irradiation time-volume histogram and the corresponding histogram(s) generated as part of the radiation treatment plan during the treatment planning process. That is, a comparison can be made between the dose rate-volume histogram and/or the irradiation time-volume histogram generated during treatment of a patient and the respective histogram that was predicted based on the prescribed radiation treatment plan.

In block 1214, in an embodiment, adjustments can be made to, for example, the beam direction and/or the beam direction based on the comparison (feedback) of block 1212.

While the operations in FIGS. 8, 10, 11, and 12 are presented as occurring in series and in a certain order, the present invention is not so limited. The operations may be performed in a different order and/or in parallel, and they may also be performed in an iterative manner. As noted above, because of the different parameters that need to be considered, the range of values for those parameters, the interrelationship of those parameters, the need for treatment plans to be effective yet minimize risk to the patient, and the need to generate high-quality treatment plans quickly, the use of the optimizer model 150 executing consistently on the computer system 100 (FIG. 1) for radiation treatment planning as disclosed herein is important.

In summary, embodiments according to the invention improve radiation treatment planning and the treatment itself by expanding FLASH RT to a wider variety of treatment platforms and target sites. Treatment plans generated as described herein are superior for sparing normal tissue from radiation during the treatment in comparison to conventional techniques even for non-FLASH dose rates by reducing, if not minimizing, the magnitude (and the integral in some cases) of the dose to normal tissue (outside the target) by design. When used with FLASH dose rates, management of patient motion is simplified because the doses are applied in a short period of time (e.g., less than a second). Treatment planning, while still a complex task of finding a balance between competing and related parameters, is simplified relative to conventional planning. The techniques described herein may be useful for stereotactic radiosurgery as well as stereotactic body radiotherapy with single or multiple metastases.

In addition to radiation therapy techniques in which the intensity of the particle beam is either constant or modulated across the field of delivery, such as IMRT and IMPT, embodiments according to the invention can be used in spatially fractionated radiation therapy including high-dose spatially fractionated grid radiation therapy and microbeam radiation therapy.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A radiation treatment system, comprising:
a beam system that generates a beam;
a nozzle coupled to the beam system and that directs the beam to a target volume; and
a control system coupled to the beam system and to the nozzle, the control system comprising a computer system comprising a processor and a memory coupled to the processor;
wherein the memory stores a radiation treatment plan comprising a dose rate-volume histogram for the target volume, wherein the dose rate-volume histogram indicates a percentage of the target volume that receives a respective dose rate; and
wherein the beam system and the nozzle are controlled by the control system according to the radiation treatment plan.

2. The radiation treatment system of claim 1, wherein the target volume comprises a plurality of sub-volumes, wherein the radiation treatment plan further comprises a dose rate-volume histogram for each sub-volume of the sub-volumes.

3. The radiation treatment system of claim 1, wherein the radiation treatment plan further comprises a number of irradiations of the target volume, a duration of each of the irradiations, and a dose deposited in each of the irradiations.

4. The radiation treatment system of claim 3, wherein the radiation treatment plan further comprises a period of time during which the irradiations are applied, and an interval of time between each period of irradiations.

5. The radiation treatment system of claim 1, wherein the radiation treatment plan further comprises directions of the beam relative to the target volume, and a beam energy for the beam.

6. The radiation treatment system of claim 1, wherein the beam comprises a type of beam selected from the group consisting of: proton; electron; photon; atom nuclei; and ion.

7. The radiation treatment system of claim 1, wherein the radiation treatment plan further comprises isolines of dose rates relative to the target volume based on the dose rate-volume histogram.

8. The radiation treatment system of claim 1, wherein the radiation treatment plan further comprises an irradiation time-volume histogram for the target volume, wherein the irradiation time-volume histogram indicates a percentage of the target volume that is irradiated for a respective length of time.

9. A method of using a radiation treatment system, the method comprising:
generating a beam with a beam system;
directing the beam at a target volume with a nozzle coupled to the beam system; and
controlling the beam with a control system comprising a computer system comprising a processor and a memory coupled to the processor, wherein said controlling is according to a radiation treatment plan stored in the memory, wherein the radiation treatment plan comprises a dose rate-volume histogram for the target volume, and wherein the dose rate-volume histogram indicates a percentage of the target volume that receives a respective dose rate.

10. The method of claim 9, wherein the target volume comprises a plurality of sub-volumes, wherein the radiation treatment plan further comprises a dose rate-volume histogram for each sub-volume of the sub-volumes.

11. The method of claim 9, wherein the radiation treatment plan further comprises a number of irradiations of the target volume, a duration of each of the irradiations, and a dose deposited in each of the irradiations, a period of time during which the irradiations are applied, an interval of time between each period of irradiations, directions of the beam relative to the target volume, and a beam energy for the beam.

12. The method of claim 9, wherein the beam comprises a type of beam selected from the group consisting of: proton; electron; photon; atom nuclei; and ion.

13. The method of claim 9, wherein the radiation treatment plan further comprises isolines of dose rates relative to the target volume based on the dose rate-volume histogram.

14. The method of claim 9, wherein the radiation treatment plan further comprises an irradiation time-volume histogram for the target volume, wherein the irradiation time-volume histogram indicates a percentage of the target volume that is irradiated for a respective length of time.

15. A method of using a radiation treatment system, the method comprising:

generating a beam with a beam system;

directing the beam at a target volume with a nozzle coupled to the beam system, wherein the target volume comprises a plurality of sub-volumes;

monitoring, with a control system coupled to the beam system, values of parameters, the values comprising a number of irradiations of each sub-volume of the plurality of sub-volumes, a duration of each of the irradiations for said each sub-volume, and a dose deposited in said each sub-volume, that result from said directing;

determining a dose rate for said each sub-volume using the values of the parameters; and determining a dose rate-volume histogram for the target volume using the dose rate for said each sub-volume, wherein the dose rate-volume histogram indicates a percentage of the target volume that receives a respective dose rate.

16. The method of claim 15, further comprising determining a dose rate-volume histogram for said each sub-volume.

17. The method of claim 15, wherein the values of the parameters further comprise a period of time during which the irradiations are applied, an interval of time between each period of irradiations, directions of the beam relative to the target volume, and a beam energy for the beam.

18. The method of claim 15, wherein the beam comprises a type of beam selected from the group consisting of: proton; electron; photon; atom nuclei; and ion.

19. The method of claim 15, further comprising determining isolines of dose rates relative to the target volume based on the dose rate-volume histogram.

20. The method of claim 15, further comprising determining an irradiation time-volume histogram for the target volume, wherein the irradiation time-volume histogram indicates a percentage of the target volume that is irradiated for a respective length of time.

* * * * *